US012790379B2

(12) United States Patent
Potter et al.

(10) Patent No.: US 12,790,379 B2
(45) Date of Patent: Nov. 10, 2026

(54) METHODS AND COMPOSITIONS FOR THE TREATMENT OF VIRAL DISEASE USING GRANULOCYTE-MACROPHAGE COLONY-STIMULATING FACTOR (GM-CSF)

(71) Applicant: THE REGENTS OF THE UNIVERSITY OF COLORADO, A BODY CORPORATE, Denver, CO (US)

(72) Inventors: Huntington Potter, Denver, CO (US); Timothy Boyd, Johnstown, CO (US); Penny Clarke, Golden, CO (US); Kenneth L. Tyler, Denver, CO (US); Lon Kendall, Bellvue, CO (US); Sarah Stonedahl, Thornton, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 911 days.

(21) Appl. No.: 17/946,816

(22) Filed: Sep. 16, 2022

(65) Prior Publication Data

US 2023/0085071 A1 Mar. 16, 2023

Related U.S. Application Data

(63) Continuation of application No. PCT/US2021/023134, filed on Mar. 19, 2021.

(60) Provisional application No. 62/992,751, filed on Mar. 20, 2020.

(51) Int. Cl.
*C07K 14/535* (2006.01)
*A61P 31/12* (2006.01)

(52) U.S. Cl.
CPC ............ *C07K 14/535* (2013.01); *A61P 31/12* (2018.01)

(58) Field of Classification Search
None
See application file for complete search history.

(56) References Cited

U.S. PATENT DOCUMENTS 5,626,617 A 5/1997 Brewitt
6,309,632 B1 10/2001 Agosti
2003/0100498 A1* 5/2003 Echols ................. A61K 38/193 424/278.1
2007/0048255 A1 3/2007 Hunter
2010/0015217 A1 1/2010 Fiala
2014/0193506 A1* 7/2014 Shams ................. A61K 38/193 424/85.1
2016/0046687 A1* 2/2016 Galipeau ............ A61K 40/4271 435/320.1

FOREIGN PATENT DOCUMENTS

WO WO-2021/188883 A1 9/2021

OTHER PUBLICATIONS

Wang et al. (Cell Research (2020) 30:269-271) (Year: 2020).*
Harvard Health Publishing (Coronavirus Resource Center; Feb. 28, 2020) (Year: 2020).*
Lang, F. M. et al., "GM-CSF-based treatments in COVID-19: reconciling opposing therapeutic approaches," Nature Reviews / Immunology, vol. 20, Aug. 2020, pp. 507-514.
Subramaniam, R. et al., "Delivery of GM-CSF to Protect against Influenza Pneumonia," PLOS One, DOI: 1371/joumal.pone. 0124593, Apr. 29, 2015, pp. 1-16.
Huang, H. et al., "Protective effects of recombinant human granulocyte macrophage colony stimulating factor on H1N1 influenza virus-induced pneumonia in mice", Cytokine, vol. 51, No. 2, Aug. 1, 2010, pp. 151-157.
Gov Clinicaltrials et al., "Sargramostim in Patients With Acute Hypoxic Respiratory Failure Due to COVID-19 (SARPAC) (SARPAC)", Mar. 30, 2020, XP093134102, Retrieved from the Internet: URL:https:// clinicaltrials.gov/study/NCT04326920?tab=table.
Partner Therapeutics, "Partner Therapeutics Announces $35 Million Contract with U.S. Department of Defense for Advanced Development and Emergency Use of Leukine® (rhuGM-CSF) for COVID-19 Acute Hypoxemic Respiratory Failure (AHRF)", Aug. 4, 2020, Retrieved from the Internet: URL:https://www.partnertx.com/partne••therapeutics-announces-35-million-contract-with-u-s-department-of•defense-for-advanced-development-and-emergency-use-of-leukine-rhugm•csf-for-covid-1 9-acute-hypoxe m ic-respi ratory-fai/.
Database Embase [Online] Elsevier Science Publishers, Amsterdam, NL; Apr. 6, 2012, 2 pages.
Chen, H. et al., "Suppressive effects on the Immune Response and Protective Immunity to a JEV DNA Vaccine by Co-administration of a GM-CSF-Expressing plasmid in Mice", PLOS One, vol. 7, No. 4, Apr. 6, 2012, pp. 1-14.

(Continued)

*Primary Examiner* — Sergio Coffa
(74) *Attorney, Agent, or Firm* — Foley Hoag LLP; Hathaway P. Russell; Ariana D. Harris

(57) ABSTRACT

Embodiments herein relate to novel compositions and methods for treating viral infections and viral infection-related conditions. In some embodiments, compositions include, but are not limited to, at least one pro-inflammatory cytokine. In accordance with these embodiments, a proinflammatory cytokine can include Granulocyte Macrophage Colony Stimulating Factor (GM-CSF) alone or in combination with other agents administered separately or together. In some embodiments, compositions including GM-CSF can be administered to a subject exposed to, suspected of having been exposed to, or having a viral infection. In other embodiments, the compositions treat, ameliorate or prevent a complication related to viral infection including, but not limited to, a central nervous system infection or condition and a lung infection or condition.

10 Claims, 4 Drawing Sheets

(56) References Cited

OTHER PUBLICATIONS

International Search Report and Written Opinion for International Application No. PCT/US21/23134 dated Jun. 8, 2021.

Supplementary European Search Report for EP Application No. 21770619.1 dated Mar. 6, 2024.

* cited by examiner

Product-Limit Survival Fit

Survival Plot

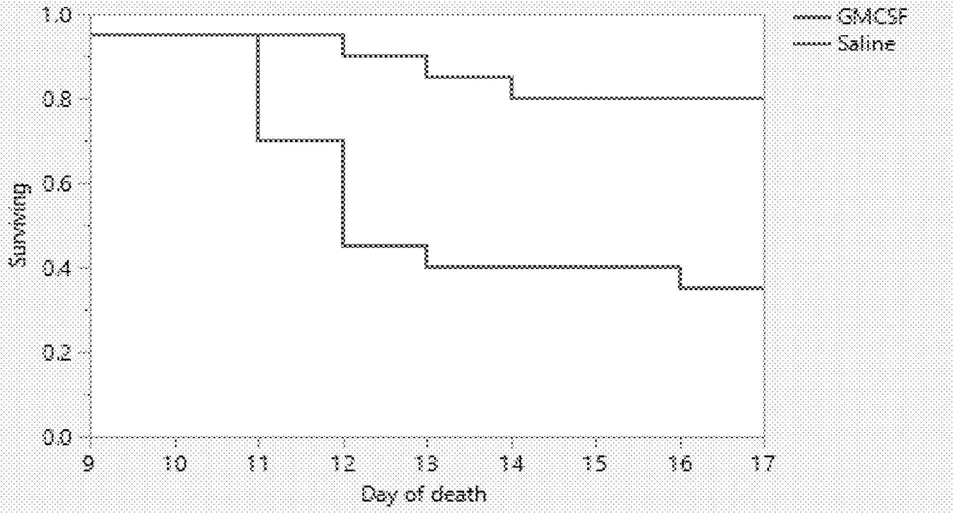

Time to event: Day of death
Censored by Censored?
Censor Code 1
Grouped by Group

Summary

| Group | Number failed | Number censored | Mean | | Std Error |
|---|---|---|---|---|---|
| GMCSF | 4 | 16 | 13.6 | Biased | 0.29889 |
| Saline | 13 | 7 | 13.25 | Biased | 0.55014 |
| Combined | 17 | 23 | 14.225 | Biased | 0.37783 |

Quantiles

| Group | Median Time | Lower 95% | Upper 95% | 25% Failures | 75% Failures |
|---|---|---|---|---|---|
| GMCSF | . | . | . | . | . |
| Saline | 12 | 11 | . | 11 | . |
| Combined | . | 13 | . | 12 | . |

Tests Between Groups

| Test | ChiSquare | DF | Prob>ChiSq |
|---|---|---|---|
| Log-Rank | 8.5672 | 1 | 0.0034* |
| Wilcoxon | 8.6394 | 1 | 0.0033* |

GMCSF

Saline

Combined

FIG. 2

METHODS AND COMPOSITIONS FOR THE TREATMENT OF VIRAL DISEASE USING GRANULOCYTE-MACROPHAGE COLONY-STIMULATING FACTOR (GM-CSF)

PRIORITY

This application is a continuation of International Application No. PCT/US2021/023134 filed Mar. 19, 2021, entitled Methods and Composition for the Treatment of Viral Disease Using Granulocyte-Macrophage Colony-Stimulating Factor (GM-CSF), which application claims priority to U.S. Provisional Application No. 62/992,751 filed Mar. 20, 2020 entitled, Methods and Composition for the Treatment of Viral Disease. This provisional application is incorporated herein by reference in its entirety for all purposes.

FIELD

Embodiments herein relate to novel compositions and methods for treating viral infections and viral infection-related conditions. In certain embodiments, the virus includes, but is not limited to, corona virus, flavivirus, alphavirus, influenza virus or other virus. In some embodiments, compositions include, but are not limited to, at least one pro-inflammatory and innate immune system stimulating cytokine(s). In accordance with these embodiments, a proinflammatory, innate immune system stimulating cytokine(s) can include Granulocyte Macrophage Colony Stimulating Factor (GM-CSF) alone or in combination with other agents administered separately or together. In certain embodiments, the GM-CSF includes recombinant GM-CSF (e.g. sargramostim). In some embodiments, compositions including GM-CSF can be administered to a subject exposed to, suspected of having been exposed to, or having a viral infection. In other embodiments, the compositions treat, ameliorate or prevent a complication related to viral infection including, but not limited to, a central nervous system infection or condition.

BACKGROUND

Viral infections are a significant cause of worldwide morbidity and mortality. For example, viral encephalitis, viral meningitis, viral encephalomyelitis, virus associated encephalopathy, virus induced demyelination and viral pneumonia represent growing concerns for global human health. These infections are on the rise especially with the increasing number of severe illnesses and deaths linked to infections of the SARS coronavirus-2, the cause of the COVID-19 global pandemic.

Recent studies have found that viral infection of the brain induces neuroinflammation, including activation of astrocytes that is characterized by changes in astrocyte morphology and increased expression of glial fibrillary acid protein (GFAP), which was attributed to increased interferon signaling, and subsequently results in astrocytic apoptosis. Subsequent studies demonstrated that depletion of microglia, the resident immune cells of the CNS that play an important role in viral clearance, resulted in increased mortality and viral titer in the brain following certain viral infections.

West Nile virus (WNV) is a leading cause of epidemic viral encephalitis and therefore, a substantial health concern. While most infections with WNV are asymptomatic or result in West Nile Fever, a small percentage of infections can result in a severe neurological disease such as encephalitis or meningitis. Mortality in patients with WNV neuroinvasive disease is about 10% and about 50% of recovering patients experience long term setback related to paralysis and memory loss and other symptoms.

Similarly, respiratory viruses, such as influenza A and corona virus continue to be leading causes of morbidity and mortality around the globe. These viruses can also invade the brain. Few effective treatment options currently exist for viral infection-related infections of the CNS or viral respiratory conditions, and the rate of mortality is on the rise. In many situations, treatment for these conditions focus on supportive care and antibiotic therapy for associated bacterial infections while the underlying viral infections runs its course.

SUMMARY

Embodiments disclosed herein relate to novel and unexpected compositions and methods for treating viral infections and viral infection-related conditions. In some embodiments, the composition includes, but is not limited to, at least one pro-inflammatory, innate immune system stimulating cytokine. In accordance with these embodiments, a proinflammatory, innate immune system stimulating cytokine can include Granulocyte Macrophage Colony Stimulating Factor (GM-CSF) alone or in combination with other agents to reduce onset of, reduce progression of or treat a viral infection in a subject. In some embodiments, a composition including GM-CSF can be administered before, at the time of, or after, or before administration of another agent used to treat or prevent a viral infection in a subject.

In some embodiments, the GM-CSF includes, but is not limited to, recombinant GM-CSF. In certain embodiments, the GM-CSF includes, but is not limited to human recombinant GM-CSF. In certain embodiments, GM-CSF can include human recombinant GM-CSF including, but not limited to, sargramostim, molgramostim, regramostim or other recombinant mammalian protein (e.g. made in mammalian cells, yeast or bacteria). In other embodiments, GM-CSF can be provided by exogenous administration of a viral or plasmid vector or mRNA construct designed to encode GM-CSF when administered to the subject using genetic engineering or other techniques known in the art. In some embodiments, compositions including GM-CSF can be administered to a subject exposed to, suspected of having been exposed to, or having a viral infection. In certain embodiments, compositions disclosed herein include combination compositions of GM-CSF and an anti-microbial agent or other pro-inflammation modulating agent.

In other embodiments, the subject exposed to a virus, or having a viral infection can be treated by compositions disclosed herein on the day of, or within days of exposure, or within days of having or diagnosis of having a viral infection. In some embodiments, compositions including GM-CSF of use to prevent, ameliorate, or treat a viral infection in a subject can be used alone or before, during or after other standard treatments. In other embodiments, compositions disclosed herein can be combination compositions including, GM-CSF and/or one or more anti-microbial agents and/or one or more additional pro-inflammatory cytokine agents delivered simultaneously. In certain embodiments, combination compositions can be delivered by injection and/or intranasally by inhalation. In certain embodiments, a subject can be initially treated with a composition including, but not limited to, GM-CSF followed by one or more anti-microbial agents and/or anti-inflammatory agents.

In some embodiments, subjects contemplated herein can be a human (e.g. adult, adolescent, child, infant or fetus) or non-human animal such as a pet or livestock or other animal exposed to or having a viral infection. In certain embodiments, the subject has been diagnosed with a viral infection. In some embodiments, compositions and methods disclosed herein can include administration of about 250 μg/m$^2$/day of GM-CSF, recombinantly produced molecule thereof or fragment or analog thereof in a single dose or multiple doses. In other embodiments, a recombinantly produced molecule or fragment thereof can be administered in a composition at a significantly lower concentration such as about 2.5 μg/m$^2$/day to about 500 μg/m$^2$/day of GM-CSF depending on potency and desired outcome, in a single or multiple treatments in a day. In certain embodiments, GM-CSF can include human recombinant GM-CSF, sargramostim, molgramostim, or regramostim or other recombinant protein or protein fragment or truncated protein. In other embodiments, exogenous administration of a viral or plasmid vector or mRNA construct designed to encode GM-CSF can be administered and expressed in the subject. In some embodiments, viral titer can be reduced in a subject receiving such a treatment compared viral titer of the subject not receiving GM-CSF, a recombinantly produced molecule thereof or fragment or analog thereof. In some embodiments, compositions and methods disclosed herein can stop the progression of or reduce viral infections in the subject relative to a subject not receiving such a treatment. In other embodiments, compositions and methods disclosed herein for treating a diagnosed viral infection (e.g. SARS, COVID-19, MERS, encephalitis, pneumonia, WNV, etc.) with GM-CSF, a recombinantly produced molecule or fragment thereof, or an analog thereof can reduce or eliminate viral titer in the subject relative a similar subject not receiving such a treatment, for example viral titer in the brain and other tissues and organs. In some embodiments, compositions and methods for administering GM-CSF, a recombinantly produced molecule or fragment thereof, or an analog thereof to a subject can increase innate immunity in the subject relative to a subject not receiving such a composition.

In certain embodiments, the virus of a viral infection to be treated by compositions and methods disclosed herein is a pathogenic virus. In other embodiments, the virus includes, but is not limited to, corona virus, flavivirus, alphavirus, enterovirus, rhabdovirus, bunyavirus, paramyxovirus, arenavirus, herpesvirus, influenza virus or other pathogenic virus that infect humans and other mammals. In some embodiments, the virus includes, but is not limited to, Severe acute respiratory syndrome-related (SARS), coronavirus (SARS-CoV), SARS-CoV-2 (COVID-19), MERS-CoV, Japanese encephalitis virus (JEV), dengue virus (serotype 1, 2, 3 and 4), West Nile virus (WNV), Zika virus, Chikungunya virus (CHIK), Murray Valley encephalitis virus (MVE), Kunjin virus, Rubeola virus, Rubella virus, cytomegalovirus. Epstein-Barr virus (EBV), varicella zoster virus, herpes simplex virus type 1, herpes simplex virus type 2, caoxsackievirus, poliovirus, echovirus, human immunodeficiency virus 1 (HIV-1), human immunodeficiency virus 2 (HIV-2), Reovirus, rabies virus, Enterovirus 71 (EV71), tick-borne encephalitis, Nipah henipavirus, Hendra virus (HeV), eastern equine encephalitis, Venezuelan equine encephalitis, western equine encephalitis, La Crosse encephalitis virus (LACV), Saint Louis encephalitis virus, lymphocytic choriomeningitis mammarenavirus (LCMV), Junin virus (JUNV), or other subtype or strain thereof or other enveloped or non-enveloped, RNA or DNA pathogenic virus capable of infecting the lungs and/or brain of its host or other pathogenic virus capable of causing an infection or secondary infection or viral infection-related condition such as pneumonia or encephalitis.

In certain embodiments, the present disclosure can include a kit of use for treating and/or preventing viral infections in a subject. In some embodiments, kits disclosed herein can include a composition including but not limited to, GM-CSF, a recombinantly produced molecule or fragment thereof, or an analog thereof and optionally, a second anti-microbial agent and at least one container.

BRIEF DESCRIPTION OF THE DRAWINGS

The following detailed description of specific embodiments of the invention will be better understood when read in conjunction with the appended drawings. For the purpose of illustrating the invention, exemplary embodiments are shown in the drawings. It should be understood, however, that the invention is not limited to the precise arrangements and instrumentalities of the embodiments shown in the drawings.

FIG. 2 is a representative graph illustrating numerical and statistical data for the exemplary methods illustrated in FIG. 1 of some embodiments disclosed herein.

DETAILED DESCRIPTION

Definitions

Figure 1:
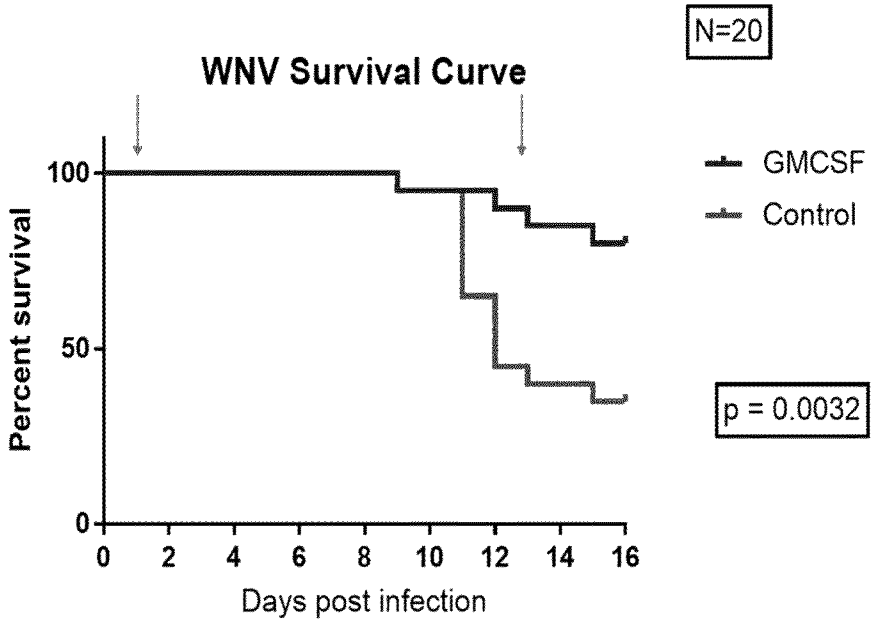
FIG. 1 is a representative a graph illustrating that treating a subject with compositions containing GM-CSF improves the survival in an animal model of West Nile virus (WNV) of some embodiments disclosed herein.

As used herein the term "about" when referring to a measurable value such as an amount, a temporal duration, and the like, can include variations of +10%, or +5%, or +1%, or +0.1% from the specified value, as such variations can be appropriate to perform the disclosed methods.

As used herein "effective amount" or "therapeutically effective amount" can be used interchangeably, and refer to an amount of a compound such as an active agent, formulation, material, or composition, as described herein able to achieve a particular biological effect or provide a therapeutic or prophylactic benefit. For example, an effective amount includes, but is not limited to, desired anti-viral effects as determined by any means suitable in the art.

As used herein, "treatment," "therapy," "treatment regimen" and/or "therapy regimen" can refer to an intervention made in response to a condition, disease, disorder or physiological condition manifested by a subject or to which a subject can be susceptible. The aim of treatment includes the alleviation or prevention of symptoms, slowing or stopping the progression or worsening of a condition, disease, disorder, infection and/or the remission of the condition, disease or disorder.

As used herein, "prevent," "prevention," "eliminate the risk" can refer to completely eliminating, or preventing, or delaying the onset of a particular disease condition, disorder or physiological condition related to the disease or condition, or to the reduction of the degree of severity of a condition related to a particular disease, disorder or physiological condition such as viral infection, relative to the time and/or degree of onset or severity in the absence of intervention using compositions disclosed in certain embodiments disclosed herein.

As used herein, "modulating," can mean mediating a detectable increase or decrease in the level of a response in a subject compared with the level of response in the subject in the absence of a treatment or compound, and/or compared with a level of a response in an otherwise identical but untreated subject. The term encompasses mediating a beneficial therapeutic response in a subject.

Unless otherwise defined, all technical terms used herein have the same meaning as commonly understood by one of ordinary skill in the art to which this disclosure belongs.

DETAILED DESCRIPTION

In the following sections, certain exemplary compositions and methods are described in order to detail certain embodiments of the invention. It will be obvious to one skilled in the art that practicing the certain embodiments does not require the employment of all or even some of the specific details outlined herein, but rather that concentrations, times and other specific details can be modified through routine experimentation. In some cases, well known methods, or components have not been included in the description.

Embodiments disclosed herein relate to novel and unexpected compositions and methods for treating viral infections and viral infection-related conditions. A need exists for therapies that treat viral infection and viral infection-related conditions or side effects including, but not limited to, those that cause encephalitis, other neurological disorders or conditions, and/or upper and/or lower respiratory conditions. Embodiments disclosed herein address these issues. In some embodiments, the composition of use to treat, ameliorate or prevent, a viral infection includes, but is not limited to, at least one pro-inflammatory, innate immune system stimulating cytokine. In accordance with these embodiments, a proinflammatory, innate immune system stimulating cytokine can include Granulocyte Macrophage Colony Stimulating Factor (GM-CSF) alone or in combination with other agents to reduce onset of, reduce progression of or treat a viral infection in a subject. It is noted that it is counterintuitive that a pro-inflammatory cytokine (e.g. GM-CSF) can be used as disclosed herein to treat, ameliorate and/or prevent viral infections alone or in combination with other treatments with improved outcomes.

In some embodiments, the GM-CSF includes, but is not limited to, recombinant GM-CSF. In certain embodiments, the GM-CSF includes, but is not limited to human recombinant GM-CSF. In certain embodiments, GM-CSF can include human recombinant GM-CSF, including, but not limited to, sargramostim, molgramostim, or regramostim or other recombinant. In other embodiments, exogenous administration of a viral or plasmid vector or mRNA construct designed to encode GM-CSF can be administered and expressed in the subject. In some embodiments, the GM-CSF includes, but is not limited to other non-human mammalian recombinant GM-CSF (e.g. for a pet or livestock or other animal). In some embodiments, compositions including GM-CSF can be administered to a subject exposed to, suspected of having been exposed to, or having a viral infection. In certain embodiments, compositions disclosed herein include combination compositions of GM-CSF and an anti-microbial agent or other pro-inflammation modulating agent (e.g. capable of inducing certain cytokines to reduce or inhibit viral infections and/or induce the immune system to fight viral infection or side effects of viral infection).

In some embodiments, subjects contemplated herein can be a human (e.g. adult, adolescent, child, infant or fetus) or non-human animal such as a pet (e.g. dog, cat, pig, rabbit) or livestock or other animal exposed to or having a viral infection. In certain embodiments, the subject has been diagnosed with a viral infection. In certain embodiments, the subject has been diagnosed as having or is suspected of developing a viral infection as a result of having or suspected of having been exposed to a virus. In some embodiments, viral titer can be reduced in a subject receiving such a treatment compared to viral titer of the subject not receiving a composition including, but not limited to, GM-CSF, a recombinantly produced molecule thereof or fragment or analog thereof. In some embodiments, compositions and methods herein can include administration of about 50 $\mu g/m^2$/day to about 1000 $\mu g/m^2$/day; about 100 $\mu g/m^2$/day to about 750 $\mu g/m^2$/day; about 150 $\mu g/m^2$/day to about 600 $\mu g/m^2$/day; about 200 $\mu g/m^2$/day to about 500 $\mu g/m^2$/day; about 200 $\mu g/m^2$/day to about 400 $\mu g/m^2$/day; or about 250 $\mu g/m^2$/day of GM-CSF, recombinantly produced molecule thereof or fragment or analog thereof in a single treatment or multiple treatments per day. In other embodiments, a subject can be treated every other day, 2 times per week, once a week or other dosing regimen such as a periodic regimen. In some embodiments, compositions and methods herein can include administration of about 250 $\mu g/m^2$/day of GM-CSF, recombinantly produced molecule thereof or fragment or analog thereof in a single dose or multiple doses. In some embodiments, two doses can be provided to the subject where the total concentration of GM-CSF or analog thereof is about 50 $\mu g/m^2$/day to about 1000 $\mu g/m^2$/day or about 100 $\mu g/m^2$/day to about 500 $\mu g/m^2$/day or about 200 $\mu g/m^2$/day to about 300 $\mu g/m^2$/day or about 250 $\mu g/m^2$/day. In certain embodiments, recombinant GM-CSF can be sargramostim, molgramostim, or regramostim or other recombinant. In some embodiments, a recombinantly produced molecule or fragment thereof can be administered in a composition at a significantly lower concentration such as about 2.5 $\mu g/m^2$/day to about 500 $\mu g/m^2$/day of GM-CSF.

In other embodiments, compositions and methods can include a composition including, but not limited to, GM-CSF, a recombinantly produced molecule or fragment thereof, or an analog thereof formulated in a pharmaceutical composition, which can further include a pharmaceutically acceptable carrier or excipient. In certain embodiments, the GM-CSF is recombinantly produces and in certain embodiments, the recombinantly produced GM-CSF can be sargramostim, molgramostim, or regramostim or other recombinant. In accordance with these embodiments, the pharmaceutical composition can be administered to the subject by any means known in the art. In other embodiments, the pharmaceutical composition can be administered to the subject by inhalation, subcutaneous, intravenous, intranasal, inhalation, intra-arterially, by slow-release microparticles or timed-released formulation, by targeted deposit directly to the area of infection. In yet other embodiments, the pharmaceutical composition can be administered to the subject by inhalation, intranasal and/or subcutaneous administration. In some embodiments, the subject can be treated one time, two times, or three times daily for a period of time to reduce and or prevent viral expansion and viral transmission contemplated herein. In yet other embodiments, the pharmaceutical composition can be administered to the subject alone, in combined treatment regimens or in combination with other agents or treatments for treating, preventing or ameliorating viral infections or viral infection-related conditions in the subject. In some embodiments, compositions and methods disclosed herein can be used in combination treatments to reduce onset, prevent, reduce progression of and/or treatment the pathological entity where other treatments can include any standard treatment for the condition. For example, it is contemplated to be used in combination with other anti-microbial agents which will be beneficial to improve outcome.

Viral infections can lead to viral infections of the brain which can induce neuroinflammation due in part by an immune response to presence of the virus. These conditions can include, activation of astrocytes characterized by changes in astrocyte morphology and increased expression of glial fibrillary acid protein (GFAP), subsequently resulting in astrocytic apoptosis. Depletion of microglia, which are involved in viral clearance can lead to increased mortality due to this increase in viral titer within the brain. In certain embodiments, viral infections can cause viral encephalitis, viral meningitis, viral encephalomyelitis, virus associated encephalopathy, virus induced demyelination, or other brain-related viral infection condition and GM-CSF prevents, ameliorates or treats viral encephalitis or the other brain-related viral infection condition. In other embodiments, viral encephalitis can be caused by a number of viruses known in the art. In accordance with these embodiments, the viruses capable of causing viral encephalitis or other viral condition of the brain, neuroinvasive condition or other condition of the central nervous system (CNS), can be, but are not limited to, West Nile virus (WNV), SARS-CoV-2 virus, Japanese encephalitis virus (JEV), Murray Valley encephalitis virus (MVE), Kunjin virus, Rubeola virus, Rubella virus, adenovirus, cytomegalovirus. Epstein-Barr virus (EBV), varicella zoster virus, herpes simplex virus type 1, herpes simplex virus type 2, caoxsackievirus, poliovirus, echovirus, human immunodeficiency virus 1, human immunodeficiency virus 2, Reovirus, Zika virus, rabies virus, Enterovirus 71 (EV71), tick-borne encephalitis, Nipah henipavirus, Hendra virus (HeV), eastern equine encephalitis, Venezuelan equine encephalitis, western equine encephalitis, La Crosse encephalitis virus (LACV), Saint Louis encephalitis virus, lymphocytic choriomeningitis mammarenavirus (LCMV), Junin virus (JUNV), or other enveloped or non-enveloped, RNA or DNA pathogenic virus and many other viruses. For example, COVID-19 is characterized in part by neurological side effects related to the ability of the SARS-CoV-2 virus to enter and infect the brain. As disclosed herein and contemplated herein, GM-CSF treatment can treat these conditions and for example, is capable of reversing related cognitive impairment, reduce viral titer with a concomitant reversal of GFAP-indicative astrogliosis.

In other embodiments, GM-CSF has been identified as playing an important role in the pathogenesis of viral lung infections. It was demonstrated that GM-CSF signaling via genetic knock-out increases susceptibility to viral lung infection. It was demonstrated that increased levels compared to control levels of GM-CSF in lung airways induces resistance to infection in viral pneumonia. In other embodiments, GM-CSF treatments were further able to increase resistance to infection in viral pneumonia in the presence of bacterial co-infection. In some embodiments, a composition including, but not limited to, GM-CSF delivered by inhalation is capable of treating pulmonary alveolar proteinosis (PAP), a condition caused by accumulation of surfactant in lung tissues due to impaired GM-CSF signaling. In accordance with these embodiments, administration of inhaled GM-CSF in a composition to treat, ameliorate or prevent onset of COVID-19 is contemplated herein.

In certain embodiments, viral infections can lead to respiratory complications or conditions, including viral pneumonia or other compromising lung condition. In certain embodiments, the viral pneumonia can be caused by Severe acute respiratory syndrome-related (SARS) coronavirus (SARS-CoV), Middle East respiratory syndrome (MERS) coronavirus (MERS-CoV), Severe acute respiratory syndrome coronavirus 2 (SARS-CoV-2), Orthomyxoviridae, Influenza virus A, Influenza virus B, Influenza virus C, Influenza virus D, Paramyxoviridae, Human parainfluenza virus, Human orthopneumovirus, Human metapneumovirus (hMPV), Epstein-Barr virus (EBV), Cytomegalovirus, other enveloped or non-enveloped, RNA or DNA pathogenic virus capable of infecting the lungs or brain of its host, among others. In some embodiments, compositions containing GM-CSF alone or in combination can be used to prevent, ameliorate or treat viral infection-related respiratory conditions.

In other embodiments, the subject exposed to a virus, or having a viral infection can be treated by compositions disclosed herein on the day of, or within days of exposure, or within days of having or diagnosis of a viral infection. In some embodiments, compositions including GM-CSF of use to prevent, ameliorate or treat a viral infection in a subject can be used alone or before, during or after other standard treatments known in the art. In other embodiments, compositions disclosed herein can be combination compositions including, GM-CSF and/or one or more anti-microbial agents and/or one or more additional pro-inflammatory cytokine agents or pro-inflammation modulating agent. In certain embodiments, a subject can be initially treated with a composition including, but not limited to, GM-CSF followed by one or more anti-microbial agents and/or anti-inflammatory agents or innate immunity boosting agents. In other embodiments, compositions disclosed herein can be administered intranasally in order to quickly provide GM-CSF to the brain of a subject or if needed the GM-CSF can be conjugated to a transporter for delivery to the brain or spinal region. In other embodiments, compositions disclosed herein can be administered by inhalation in order to quickly provide GM-CSF compositions to the lung. In yet other embodiments, compositions disclosed herein can be administered either subcutaneously or intravenously for a more systemic effect to prevent, ameliorate or treat viral infections contemplated herein. In accordance with these embodiments, the compositions delivered by any acceptable mode can reduce viral titer, prevent or ameliorate viral infection and/or side effects of viral infection.

In certain embodiments, the virus of a viral infection to be treated by compositions and methods disclosed herein is a pathogenic virus. In other embodiments, the virus includes, but is not limited to, corona virus, flavivirus, alphavirus, influenza virus or other pathogenic virus that infect humans and other mammals. In some embodiments, the virus includes, but is not limited to, Severe acute respiratory syndrome-related (SARS), coronavirus (SARS-CoV), SARS-CoV-2 (COVID-19), Japanese encephalitis virus (JEV), dengue virus (serotype 1, 2, 3 and 4), West Nile virus (WNV), Zika virus, Chikungunya virus (CHIK), Murray Valley encephalitis virus (MVE), Kunjin virus, Rubeola virus, Rubella virus, cytomegalovirus. Epstein-Barr virus (EBV), varicella zoster virus, herpes simplex virus type 1, herpes simplex virus type 2, caoxsackievirus, poliovirus, echovirus, human immunodeficiency virus 1 (HIV-1), human immunodeficiency virus 2 (HIV-2), Reovirus, rabies virus or other pathogenic virus capable of causing a respiratory-related infection or secondary infection such as pneumonia.

GM-CSF Cytokine Therapy

In certain embodiments, compositions disclosed herein include GM-CSF of use for treating, ameliorating or preventing viral infections. GM-CSF is a monomeric glycosylated polypeptide signaling molecule which is typically secreted by immune cells such as macrophages, T cells, mast cells, natural killer (NK) cells, as well as normal tissue cells such as endothelial cells and fibroblasts. In the bone marrow, GM-CSF functions as a leukocyte growth factor, and stimulates hematopoietic progenitor cells to differentiate into monocytes and granulocytes. In addition to its growth factor function, GM-CSF also acts as an important modulator of immune responses. Upon stimulation, many types of immune cells produce and secrete GM-CSF where it can act both locally to enhance maturation and antigen presentation function of macrophages and dendritic cells, as well as in a paracrine fashion in order to recruit circulating neutrophils, monocytes, and lymphocytes to areas of infection and inflammation. Clinically, GM-CSF is used to encourage bone marrow and immune cell recovery in subjects who have undergone immuno-depleting treatments; for example, radiation therapy, chemotherapy, etc.

In certain embodiments, treatments for CNS (e.g. neuroinvasive conditions) and lung diseases associated with viral infection or viral infection in conjunction with co-infection with bacteria are disclosed. In accordance with these embodiments, compositions disclosed herein are designed to reduce, inhibit or prevent viral infection in the subject. It is noted that viral encephalitis is associated with inflammation of the brain and is caused by an active viral infection. Some viral diseases, such as measles and rubella, can in some instances move from peripheral tissues into the CNS to cause encephalitis. Clinically, viral encephalitis symptoms can include high temperatures, headache, sensitivity to light, and general malaise accompanied by muscle stiffness of the neck and back. In more advanced cases, viral encephalitis can be accompanied by vomiting and changes to cognitive function including memory loss, confusion, seizures, and paralysis. In more severe cases, viral encephalitis can lead to coma and death. In certain embodiments, side effects of viral infection can cause viral induced demyelination or viral demyelination and compositions and methods disclosed herein can be used to reduce onset, prevent or treat these conditions in a subject. Current treatment options for these side effects such as viral encephalitis are few and tend to focus on supportive care to ameliorate the associated symptoms of the disease without affecting the underlying infection, including medications to reduce pain, prevent vomiting and seizures, and reduce fever. In some cases, treatment with antiviral medications, including enzyme inhibitors and nucleoside analogs, can be used if they are known to be specific for the particular virus causing the disease. Co-infection with bacteria can often be treated by antibiotics. Embodiments disclosed herein relate to treating these conditions with a GM-CSF-containing composition alone or in combination with standard treatments such as antibiotics or other anti-microbial agents.

In certain embodiments, compositions disclosed herein can be used to treat a respiratory component of a viral infection. For example, viral pneumonia is often a progressive condition in which a fever, dry cough, headache, or sore throat represent a mild version which can steadily worsen over time. One side effect, inflammation of the lungs, can often lead to accumulation of fluid in the lung tissues, which reduces lung function and leads to hypoxia. In many cases, viral pneumonia can be accompanied by a bacterial co-infection. While bacterial co-infection can often be treated by antibiotics, few specific treatments for viral pneumonia are currently available. Embodiments disclosed herein address this issue. Standard treatment focuses on supportive measures including medications to reduce fever, relieve pain, and intravenous replacement of fluids and electrolytes. Reduced lung function can be compensated by oxygen and, in serious cases, with mechanical ventilation which was commonly observed in SARS-CoV2 infections with devastating results and significant loss of life. If able, recovery from viral pneumonia can be slow can frequently be associated with long-term effects to lung function including increased risks of other respiratory-related conditions; for example, adult asthma, non-smoking related COPD, and bronchiectasis. SARS-CoV2 infections have led to a multitude of serious side effects including, respiratory side effects in all ages with severe consequences to young and older patients.

Pharmaceutical Compositions

Pharmaceutical compositions of the present invention can include pro-inflammatory cytokines as described herein, alone or in combination with one or more pharmaceutically or physiologically acceptable carriers, diluents or excipients or other standard treatment agents. Such compositions can include buffers such as neutral buffered saline, phosphate buffered saline and the like; carbohydrates such as glucose, mannose, sucrose or dextrans, chitosan and derivatives thereof such as trimethyl chitosan, mannitol; proteins, polypeptides or amino acids such as glycine; antioxidants; chelating agents such as EDTA or glutathione; adjuvants (e.g., aluminum hydroxide); and preservatives. In certain embodiments, pharmaceutical compositions disclosed herein can be formulated for intranasal, intravenous or subcutaneous administration.

Pharmaceutical compositions disclosed herein can be administered in a manner appropriate for the condition or infection to be treated (or prevented). The quantity and frequency of administration can be determined by such factors as the condition of the subject and the type and severity of the subject's viral infection or condition, although appropriate dosages may be determined by clinical trials and/or health professionals.

Compositions disclosed herein can be administered in a single administration or multiple administrations at dosages within ranges provided herein. In certain embodiments, optimal dosage and treatment regimens for a particular subject can readily be determined by one skilled in the art; for example, by monitoring the subject for exposure to a virus, signs of viral infection or viral infection progression or treatment-related toxicity and adjusting the treatment accordingly.

In certain embodiments, administration of the pro-inflammatory cytokines, recombinant molecules thereof or biologically active fragments thereof can be carried out in any manner or mode of administration known in the art. In certain embodiments, cytokines of the present invention can be administered to a subject by aerosol inhalation, by injection, ingestion, transfusion, implantation or transplantation. In accordance with these embodiments, compositions described herein can be administered to the subject transarterially, subcutaneously, intradermally, intratumorally, intranodally, intramedullary, intramuscularly, by intravenous (i.v.) injection, or intraperitoneally. In some embodiments, combination compositions including GM-CSF-containing formulations and another anti-microbial agent can be co-administered or combined before subcutaneous, intravenous and/or intranasal administration.

In certain embodiments, GM-CSF can be administered at the same time or at different times as other anti-viral or other therapies known in the art. In some embodiments, COVID-19 infections can be treated with GM-CSF alone or in combination with other anti-viral agents such as remdesivir. In certain embodiments, compositions disclosed herein can be administered early in the onset of viral infection and viral disease, followed by dexamethasone or other anti-inflammatory agent to treat or prevent side effects and conditions caused by viral infections. In yet other embodiments, compositions containing GM-CSF can be administered to a subject having a long-term neurological dysfunction caused by viral infections or other condition, including memory problems, to restore normal function.

In certain embodiments, kits are contemplated of use herein. In accordance with these embodiments, kits can include at least one container. In other embodiments, kits can include at least one composition including, but not limited to, GM-CSF. In yet other embodiments, kits can include, but are not limited to other agents such as anti-microbial agents and/or viral infection testing agents of use to test a sample obtained from a subject. In yet other embodiments, kits can include combinations of agents to treat or reduce onset of a viral infection including, but not limited to, a GM-CSF-containing composition.

The practice of embodiments of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature.

Embodiments of the present invention is further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention or the scope of the appended claims.

EXAMPLES

These Examples are provided for the purpose of illustration only, and the invention is not limited to these Examples, but rather encompasses all variations that are evident as a result of the teachings disclosed herein.

Example 1

Treatment with GM-CSF reduces viral titer in brain and improves survival of mice infected with West Nile virus In one exemplary method, two groups of 10-week-old wild-type (C57Bl/6) mice (n=20 mice per group) were first injected with 1,000 plaque-forming units (PFU) of West Nile virus (WNV) (strain TX02) subcutaneously into the footpad on day 0. Twenty-four hours later (on day 1), a treatment regimen consisting of daily subcutaneous injections of GM-CSF (5 μg) or daily subcutaneous injection with an equal volume of saline was started. Treatments continued daily for a total of 13 daily injections, with the last injection being on day 13. Mouse survival was scored over the course of the study. Moribund mice that had lost greater than 25% of their body weight (compared to their weight on the day they were injected with WNV) and/or that were showing some neurological symptoms were euthanized and scored as "non-surviving." Survival curves of the GM-CSF-treated group and of the saline-treated group are displayed in FIG. 1. These data demonstrate that treatment with GM-CSF results in a statistically significant reduction in WNV-induced death compared to treatment with saline (p value=0.0034, and the data are right censored at day post-infection [DPI] 17). Numerical and statistical data for each group are listed in the tables in FIG. 2.

FIG. 1 represents a graph illustrating that GM-CSF treatment significantly improves the survival of mice after infection with West Nile virus (WNV). Two groups of 10-week-old wild-type (C57Bl/6) mice (n=20 mice per group) were injected with 1,000 plaque-forming units (PFU) of WNV (strain TX02) into the footpad on day 0. One day after the mice were injected with WNV (on day 1), daily subcutaneous injection treatment with GM-CSF (5 μg) or daily subcutaneous injection with an equal volume of saline was started, for a total of 13 daily injections, with the last injection being on day 13. Mouse survival was scored. Moribund mice that had lost greater than 25% of their body weight (compared to their weight on the day they were injected with WNV) and/or that were showing some neurological symptoms were euthanized and scored as "non-surviving."

Figure 3A:
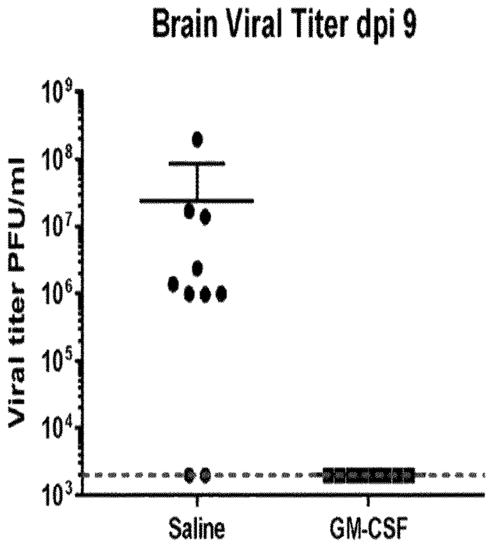
FIGS. 3A and 3B represent viral titer found in brain samples (3A) and spleen samples (3B) in a control versus treated subject of some embodiments disclosed herein.
Figure 3B:
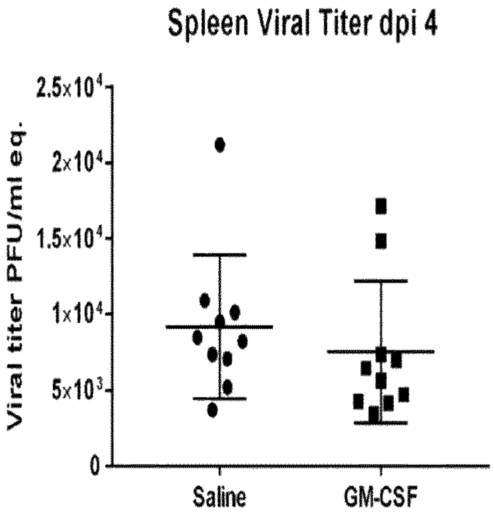

To assess viral titers in the brain and peripheral organs, mice were harvested from each treatment group of a second experiment at days 4, 6, and 9 post infection. While viral load in the brains of the control treated mice were high, there was no detectable virus in the brains of the mice in the GM-CSF treatment group indicating that GM-CSF either prevented virus from entering the brain or promoted rapid clearance of virus from the brain (FIG. 3A). Given the surprising results in the brain, samples were obtained to assess titers in peripheral organs of the test animals. Unexpectedly, viral loads in the spleen were similar between the treated and untreated mice (FIG. 3B). This observation supports a brain specific effect of GM-CSF treatment in mice infected with WNV and other related viruses that infect the brain of its subject. It was observed that GM-CSF treatment in WNV-infected mice improved survival and decreased viral replication in the CNS, reducing titers. This observation supports using GM-CSF compositions for treating individuals diagnosed with WNV neuro-invasive disease.

FIG. 3 is a graph representative that GM-CSF treatment limits viral growth in the brain but not in the spleen of WNV-infected mice. Mice were infected with 1000 pfu of the TX02 WNV strain by footpad injections and subcutaneous injections of GM-CSF or saline began 1-day post infection. Mice were sacrificed at days post infection (dpi) 4, 6, and 9 and organs were collected for viral titer analysis. Viral titers of the brains at dpi 9 were determined using plaque assays. It was found that while viral load in the brains of most of the saline treated mice was high, there was no detectable virus in the brains of the GM-CSF treated mice. Viral titers in the spleen at dpi 4 were determined using RT-qPCR and it was found that viral titers were equivalent between treatment groups in the spleen.

Methods

GM-CSF Preparation and administration: 100 ug stocks were dissolved in 4 ml of saline and 200 ul was aliquoted into syringes to be used for subcutaneous injections. The final dose was 5 μg in 200 ul saline. Mice were injected with either GM-CSF or control saline via daily subcutaneous injection.

Mice: Female 8-10-week-old C57BL/6 mice were used in the study. Mice were observed daily for signs of illness.

WNV stock and inoculation: Viruses were grown in Vero cells followed by a passage through C6/36 mosquito cells to amplify the virus. Following confirmation of cytopathic effects in vitro, the virus was purified through sucrose ultracentrifugation. Viruses were diluted to the indicated inoculums in sterile phosphate-buffered saline. Injections were performed in the left rear footpad. To determine the effect of GM-CSF treatment on mice infected with WNV, mice were inoculated with 1000 Plaque Forming Units (PFU) of the TX02 WNV strain via footpad injections. One day following infection, mice started treatment with GM-CSF or saline control by daily subcutaneous injection. Daily injections continued until day 13 post infection.

To determine the effect of GM-CSF treatment on mice infected with WNV, mice were inoculated with 1000 Plaque Forming Units (PFU) of the TX02 WNV strain via footpad injections. One day following infection, mice started treatment with GM-CSF or saline control by daily subcutaneous injection. Daily injections continued until day 13 post infection.

Plaque Assay and determination of viral titers: Vero cells (ATCC) were grown up in 125 $cm^2$ culture flasks to about confluency and then cells were transferred to 6-well-plates and grown to about 70-80% confluency. The Vero culture media is removed, and virus was placed on the cells and allowed to adsorb for 1 hour at 37 degrees Celsius. The virus was removed and an overlay containing a 1:1 ratio of 1.5% agar solution and complete media is added. The plates were then incubated at 37 degrees Celsius for 5 days. The plates were visualized using MTT staining. Plaques were counted and pfu/ml was calculated.

RT-qPCR and determination of viral titers: Whole-brain homogenates were made using a BeadBug homogenizer. About 150 ul of this homogenate was then mixed with RLT (RNA tissue lysis extraction buffer; Qiagen). RNA was extracted using the Qiagen RNeasy midikit protocol and then quantified and tested for purity on a AlphaSpec NanoDrop. Following prep, 1 μg of RNA was converted to cDNA using the Qiagen iScript kit. RT-qPCR was done on a CFX1000 instrument (Bio-Rad) and analyzed using Bio-Rad software before statistical analysis (t test) was completed using GraphPad software.

Example 2

Treatment with GM-CSF reduces viral titer in lung and brain and improves survival of mice infected with SARS-CoV-2.

In another exemplary method, to test the antiviral potential of GM-CSF in SARS-CoV-2 infection, transgenic mice were used that express the human ACE2 gene (B6.Cg-Tg (K18-ACE2)2Prlmn/J; abbreviated K18 hACE2 hereinafter) obtained from Jackson Laboratories (Stock No. 034860). Human ACE2 (hACE2) is a receptor needed for both the SARS-CoV and SARS-CoV-2 viruses to enter into cells and, when expressed in mice under the control of the keratin 18 promoter (K18), generates an animal model susceptible to infection of these human coronaviruses. This model is an acceptable SARS-CoV/CoV-2 model. Intranasal infection with SARS-CoV-2 virus results in K18-hACE2 mice with severe illness that typically reaches criteria for euthanasia at about 5-8 days post-challenge, and the K18-hACE2 strain has been used for studying both SARS-CoV and SARS-CoV-2 pathogenesis and potential therapeutics. K18 hACE2 mice were housed and treated in an approved animal facility with filtered air and a 12:12 light: dark cycle, fed a Teklad 2918 diet, and provided with water ad libitum. All procedures were approved in accordance with National Institutes of Health guidelines for the care and use of animals in research. Same-sex littermates were housed in the same cage. After the experiment was completed, mice were genotyped by polymerase chain reaction (PCR) using a protocol from the Jackson Laboratory, and all were found to harbor the hACE2 transgene as expected. Eight male and eight female mice received GM-CSF treatment; seven male and seven female mice received saline placebo for this study.

GM-CSF

GM-CSF is a monomeric glycosylated polypeptide signaling molecule which is typically secreted by immune cells such as macrophages, T cells, mast cells, natural killer (NK) cells, and other tissue cells, such as endothelial cells and fibroblasts. In the bone marrow, GM-CSF functions as a leukocyte growth factor and stimulates hematopoietic progenitor cell mobilization, proliferation, and differentiation towards monocytes, granulocytes, and dendritic cells, as well as inducing endothelial progenitor cells and other myeloid-lineage cells. In the brain, GM-CSF increases the number and activation of microglia and in addition to its growth factor function, GM-CSF acts as an important modulator of immune responses. Recombinant mouse GM-CSF was obtained.

In accordance with this example, on day 0, 30 10-week-old mice were inoculated by nasal application of 105 colony/plaque forming units (PFU) of SARS-CoV2 virus under light anesthesia. Starting 24 hours later (Day1), a treatment regimen consisting of daily subcutaneous (SC) injections of GM-CSF (200 mcg/kg in 200 μL) or daily SC injection with an equal volume of sterile saline (200 μL) was started in 16 and 14 randomly-chosen mice respectively. Treatments continued daily, with the last injection being on day 14. Mouse survival was scored over the course of the study. Moribund mice that had lost greater than 25% of their body weight (compared to their weight on the day they were injected with Sars-CoV-2) were euthanized and scored as "non-surviving." Mice that remained alive for 14 days were sacrificed. Each day, each mouse was weighed. At death or sacrifice, spleen, kidney, liver, brain, lung tissues were collected and parts frozen or fixed in fresh 4% paraformaldehyde.

Statistical Analysis

Mouse weight by Day Post-Infection (DPI) was log transformed and analyzed with longitudinal regression and spaghetti plots. Some values of virus plaque forming units (PFU) were less than detectable, and 10 PFU/100 mg of tissue was determined as the minimal detectable value so to apply a logarithmic transform. The means on the log scale these were tested for differences with a likelihood method for a mixture model. A binary event determines whether virus is present. If no virus present, then the log value of the detection threshold is assigned. If yes, virus is present, then a Gaussian distribution is assumed. Survival time was analyzed descriptively with Kaplan-Meier curves, and with a Weibull survival cure model, where a mouse can either be a long term survivor or not, and a Weibull survival distribution is assumed for the non-survivors. Statistical analysis was limited by the small sample sizes. Computations were performed in SAS 9.4.

It was demonstrated that GM-CSF treatment using this acceptable animal model at least reduced viral titer to a significant level and in other GM-CSF treatment effectively completely eliminated the virus from the lungs (and in other observations at least reduced virus levels in the brain). Therefore, GM-CSF treatment alone or in combination treatments can be used safely and effectively to treat viral infections contemplated herein.

TABLE 1

| Mouse ID | Sex | Treatment | DPI 0 | DPI 1 | DPI 2 | DPI 3 | DPI 4 | DPI 5 | DPI 6 | DPI 7 | DPI 8 |
|---|---|---|---|---|---|---|---|---|---|---|---|
| 1 | M | GMCSF | 22.1 | 22.3 | 22.3 | 22.3 | 23 | 22.6 | 22.4 | 22.6 | 22 |
| 2 | M | GMCSF | 21.4 | 21.6 | 21.4 | 21.5 | 21.5 | 20.4 | 18.36 | 17.7 | 19 |
| 3 | M | GMCSF | 21.3 | 21.2 | 21.3 | 21.6 | 19.4 | 19.6 | x | x | x |
| 4 | M | GMCSF | 20.2 | 20.7 | 21 | 21.2 | 18.6 | 17.6 | 16.6 | x | x |
| 5 | M | GMCSF | 20.8 | 19.7 | 19.8 | 19.1 | 17.2 | 16.5 | x | x | x |
| 6 | M | GMCSF | 22.1 | 21.7 | 21.7 | 21.9 | 20.2 | 19.6 | 18.5 | 19.5 | 21 |
| 7 | M | GMCSF | 20.9 | 20.2 | 20.5 | 21.1 | 21.1 | 19.6 | 18.1 | 16.8 | 16 |
| 8 | M | GMCSF | 18.4 | 17.8 | 18.3 | 18.4 | 18.1 | 17.4 | 16.4 | 15.4 | x |
| 15 | F | GMCSF | 15.8 | 15.7 | 15.6 | 15.8 | 15.4 | 13.6 | x | x | x |
| 16 | F | GMCSF | 19.2 | 19.4 | 19.2 | 19 | 18.5 | 16.4 | 15.5 | 14.1 | 15 |
| 17 | F | GMCSF | 19 | 18.3 | 18.3 | 17.8 | x | x | x | x | x |
| 18 | F | GMCSF | 15.8 | 15.6 | 15.7 | 15.7 | 15.4 | 13.6 | 12.9 | 12.2 | x |
| 19 | F | GMCSF | 17.4 | 17 | 17.1 | 16.9 | 14.7 | 13.5 | x | x | x |
| 28 | F | GMCSF | 14.9 | 14.8 | 15.5 | 15.4 | 15.2 | 14.3 | 14.2 | x | x |
| 29 | F | GMCSF | 18.2 | 17.8 | 18 | 18.5 | 17.7 | 16.8 | 15.5 | 14.6 | 15 |
| 30 | F | GMCSF | 17.6 | 17.8 | 17.8 | 17.5 | 16.2 | 15.8 | 14.5 | 13.8 | 13 |
| 9 | M | Saline | 22.1 | 21.7 | 22.5 | 22.4 | 21.3 | 20.3 | 19.2 | 19.6 | 21 |
| 10 | M | Saline | 20.1 | 19.3 | 21.2 | 20.3 | 19.1 | 17 | 16.2 | 15.5 | x |
| 11 | M | Saline | 21.1 | 21.1 | 21.6 | 21.7 | 20 | 18.1 | x | x | x |
| 12 | F | Saline | 17.6 | 16.9 | 17.2 | 17.4 | 16.8 | 15.9 | x | x | x |
| 13 | F | Saline | 15.7 | 15.3 | 15.1 | 15.2 | 13.9 | 12.8 | 11.8 | x | x |
| 14 | F | Saline | 17.2 | 17.2 | 17.1 | 17.1 | 17.3 | 15.6 | 13.7 | 14.1 | x |
| 20 | F | Saline | 17.2 | 16.2 | 16.6 | 17.1 | 15.8 | 13.7 | x | x | x |
| 21 | M | Saline | 22.7 | 22.7 | 22.4 | 22.3 | 20.9 | 19.4 | x | x | x |
| 22 | M | Saline | 19.9 | 18.7 | 19.2 | 19.4 | 17.8 | 16.9 | 15.7 | x | x |
| 23 | M | Saline | 23.9 | 22.9 | 23.4 | 24.9 | 24.8 | 24.8 | 25.3 | 25.3 | 25 |
| 24 | M | Saline | 21.7 | 21.36 | 21.2 | 21.4 | 21.5 | 21.2 | 20 | 19.8 | 20 |
| 25 | F | Saline | 17.9 | 17.8 | 17.6 | 17.8 | 18.3 | 15.8 | x | x | x |
| 26 | F | Saline | 16.9 | 16.6 | 16.6 | 16.5 | 16.5 | 16.4 | 14.9 | 14.3 | 15 |
| 27 | F | Saline | 16.1 | 15.8 | 16.3 | 16.1 | 15.8 | 14.6 | x | x | x |

| Mouse ID | Sex | Treatment | DPI 9 | DPI 10 | DPI 11 | DPI 12 | DPI 13 | DPI 14 | LCFU | BCFU |
|---|---|---|---|---|---|---|---|---|---|---|
| 1 | M | GMCSF | 22.6 | 22.3 | 22.5 | 22.7 | 22.3 | 23.4 | 0 | 0 |
| 2 | M | GMCSF | 20.8 | 21.3 | 21.8 | 22.3 | 22.8 | 23.9 | 0 | 0 |
| 3 | M | GMCSF | x | x | x | x | x | x | 78000 | 1.50E+14 |
| 4 | M | GMCSF | x | x | x | x | x | x | 44000 | 1.48E+14 |
| 5 | M | GMCSF | x | x | x | x | x | x | 180000 | 2.42E+14 |
| 6 | M | GMCSF | 21.9 | 22.3 | 22.3 | 22.4 | 22.9 | 23.2 | 0 | 0 |
| 7 | M | GMCSF | x | | x | x | x | x | 0 | 130 |
| 8 | M | GMCSF | x | x | x | x | x | x | 16000 | 3.60E+14 |
| 15 | F | GMCSF | x | x | x | x | x | x | 54000 | 2.40E+14 |
| 16 | F | GMCSF | 16.2 | 17.5 | 17.6 | 17.9 | 18.4 | 18.6 | 0 | 0 |
| 17 | F | GMCSF | x | x | x | x | x | x | 500000 | 9.00E+12 |
| 18 | F | GMCSF | x | x | x | x | x | x | 67000 | 2.40E+14 |
| 19 | F | GMCSF | x | x | x | x | x | x | 140000 | 3.64E+14 |
| 28 | F | GMCSF | x | x | x | x | x | x | 146000 | 7.90E+13 |
| 29 | F | GMCSF | 16.2 | 17 | 17.9 | 18.3 | 18.8 | 18.7 | 0 | 0 |
| 30 | F | GMCSF | 13.2 | 12.5 | x | x | x | x | 0 | 43000 |
| 9 | M | Saline | 22 | 22 | 22.1 | 22 | 22.3 | 22.7 | 0 | 0 |
| 10 | M | Saline | x | x | x | x | x | x | 42000 | 4.00E+14 |
| 11 | M | Saline | x | x | x | x | x | x | 188000 | 3.20E+14 |
| 12 | F | Saline | x | x | x | x | x | x | 500000 | 3.40E+14 |
| 13 | F | Saline | x | x | x | x | x | x | 89000 | 7.80E+12 |
| 14 | F | Saline | x | x | x | x | x | x | 80000 | 9.40E+11 |
| 20 | F | Saline | x | x | x | x | x | x | 292000 | 2.44E+14 |
| 21 | M | Saline | x | x | x | x | x | x | 500000 | 2.80E+14 |
| 22 | M | Saline | x | x | x | x | x | x | 110000 | 9.20E+11 |
| 23 | M | Saline | 25.9 | 25.6 | 25.8 | 25.7 | 25.9 | 25.9 | 0 | 0 |
| 24 | M | Saline | 21.5 | 21.4 | 21.4 | 21.4 | 21.5 | 21.7 | 0 | 0 |
| 25 | F | Saline | x | x | x | x | x | x | 26000 | 2.60E+14 |
| 26 | F | Saline | 15.9 | 16.7 | 16.9 | 17.2 | 17.6 | 17.3 | 0 | 0 |
| 27 | F | Saline | x | | | | | | | |

Table 1 illustrates some representative results of the weights and mortality of each mouse at each Day Post-Infection (DPI) and of the viral titer measured as plaque forming units (PFU) per 100 μg of lung tissue at death or sacrifice. Because the selected mouse strain is extremely sensitive to SARS-CoV-2 and individuals are expected to lose substantial weight and to die by day 5-8 from an inoculation of 105 PFU of virus, based on their not losing any weight, it appears likely that mouse #1 and mouse #23 did not get effectively infected. Table 1 illustrates data from a representative experiment that generated the curve in FIG. 4. The mice ID numbers are indicated in column 1. The treatment (GM-CSF or saline) is indicated in column 3. The weights on each day post infection are illustrate in columns labeled (DPI 0-DPI 14). The Xs indicate that the mouse died before that day. All mice still alive at DPI 14 were euthanized. The last two columns demonstrate that the number of live viruses (measured as colony-forming units; CFU) per 0.1 grams of lung tissue (LCFU) and brain tissue (BCFU) of each mouse at the time the mouse either died or was euthanized. It is unclear but one hypothesis for the lack of weight loss of two mice (#1 and 23) is that they may not have gotten infected. One mouse (#17) died immediately after treatment injection not due to infection of treatment. These three mice were not further analyzed or included in efficacy assessments which is appropriate given the study.

Figure 4:
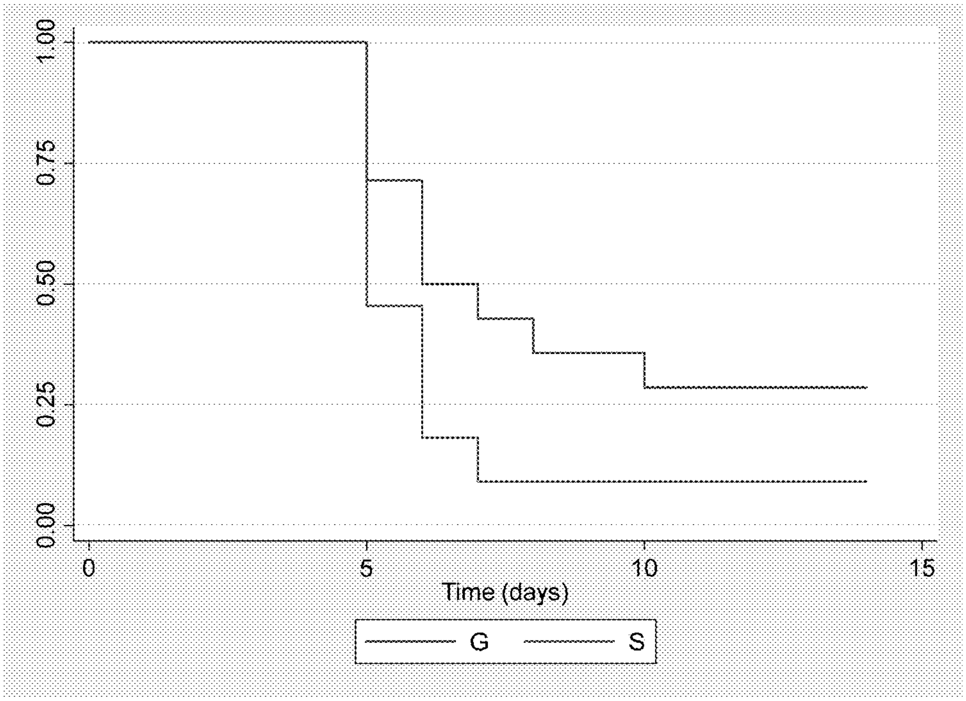
FIG. 4 is a graph of a representative survival curve of GM-CSF treated versus control treated animals of an acceptable animal model of some embodiments disclosed herein.

Kaplan-Maier survival curves of the GM-CSF-treated group and of the saline-treated group (of human ACE-2 transgenic mice infected with SARS-CoV-2) are illustrated in FIG. 4. Analysis was carried out using cure mixture model using a Weibull distribution for the time to event for the non-survivors. GM-CSF increases the odds of long-term survival, compared to saline, by an estimated 21.22% (odds ratio estimate=1.2122, 95% CI=(0.1999, 7.3507), p value=0.8285). For non-survivors, compared to saline, GM-CSF decreased the hazard of death from infection by an estimated 69.41% (hazard ratio estimate=0.3059, 95% CI=(0.1032, 0.9065), p value=0.0337), and the effect is statistically significant for univariate alpha=0.05.

These data demonstrate that treatment with GM-CSF leads to a statistically significant slowing in SARS-CoV-2-induced death in K18 hACE2 mice compared to treatment with saline and a weak statistically non-significant trend, in the benefit of GM-CSF treatment on long-term survival.

As referenced above, this mouse strain is extremely sensitive to intranasal infection with SARS-CoV-2 and an acceptable model for these infections. Because of this sensitivity to the infection, the survival of any mice that lost significant weight was unexpected.

Table 1 illustrates the viral titer in the lung and brain tissue of mice that died or were euthanized during the course of the experiment and those that were sacrificed at day 14. The findings in the lungs indicated that all mice that survived to day 14 had effectively cleared the virus (<10 PFU/100 mg tissue). Of the mice that died or were euthanized during the course of the experiment, the ones that received saline all showed a large viral titer in lung tissue. Mice treated with GM-CSF showed significantly less virus in lung tissue (including two cases, #s 7,30, with undetectable virus) compared to saline treated mice that died or were euthanized before day 14. Using 10 (the estimated lowest detectable PFU/100 mg tissue) for the '<10' values in Table 1 results in a p value of 0.0466 for a T-test on the untransformed values.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety to the extent they are not inconsistent with the explicit teachings of this specification.

What is claimed is:

1. A method for treating or ameliorating one or more viral infection-related conditions in a subject comprising, administering to the subject a composition consisting essentially of granulocyte-macrophage stimulating factor (GM-CSF), wherein the one or more viral infection-related conditions is selected from encephalitis, meningitis, encephalomyelitis, encephalopathy, virus-induced demyelinating diseases, peripheral neuropathy, and combinations thereof, thereby treating or ameliorating the viral related conditions in the subject.

2. The method according to claim 1, wherein the virus comprises one or more of corona virus, flavivirus, alphavirus, herpes virus, adenovirus, influenza virus, enterovirus, rhabdovirus, bunyavirus, paramyxovirus, arenavirus, or other enveloped or nonenveloped, DNA or RNA pathogenic virus capable of infecting at least one of lungs or brain of its host.

3. The method according to claim 1, wherein the virus comprises one or more of Severe acute respiratory syndrome-related (SARS)-CoV, SARS-CoV-2, MERSCoV, other SARS-associated coronaviruses, Japanese encephalitis virus (JEV), dengue virus (serotype 1, 2, 3 and 4), West Nile virus, Zika virus, Chikungunya virus (CHIK), Murray Valley encephalitis virus (MVE), Kunjin virus, Rubeola virus, Rubella virus, cytomegalovirus, Epstein-Barr virus (EBV), varicella zoster virus (VZV), herpes simplex virus type 1, herpes simplex virus type 2, caoxsackievirus, poliovirus, echovirus, human immunodeficiency virus I (HIV-I), human immunodeficiency virus 2 (HIV-2), Reovirus, rabies virus, Enterovirus 71 (EV71), tickborne encephalitis, Nipah henipavirus, Hendra virus (HeV), eastern equine encephalitis, Venezuelan equine encephalitis (VEE), Western equine encephalitis (WEE), La Crosse encephalitis virus (LACV), Saint Louis encephalitis virus, lymphocytic choriomeningitis mammarenavirus (LCMV), and Junin virus (JUNV).

4. The method according to claim 1, wherein administering the composition comprises administering the composition by inhalation to the subject.

5. The method according to claim 1, wherein the subject is a human and the GM-CSF is human recombinant GM-CSF.

6. The method according to claim 1, wherein the virus comprises a SARS-CoV-2 infection (COVID-19).

7. The method according to claim 1, wherein the subject treated with the composition is not treated with anti-inflammatory agents or any applicable pre-existing treatment with an anti-inflammatory agent is temporarily or completely stopped in the subject undergoing treatment with the composition.

8. The method according to claim 1, further comprising administering one or more of an anti-viral or pro-inflammatory agent to the subject.

9. The method according to claim 8, wherein the anti-viral agent comprises remdesivir.

10. The method according to claim 7, wherein the anti-inflammatory agent comprises dexamethasone.

* * * * *